(12) United States Patent
Pandey et al.

(10) Patent No.: US 8,198,432 B2
(45) Date of Patent: Jun. 12, 2012

(54) PORPHYRIN-BASED COMPOUNDS FOR TUMOR IMAGING AND PHOTODYNAMIC THERAPY

(75) Inventors: Ravindra K. Pandey, Williamsville, NY (US); Munawwar Sajjad, Clarence Center, NY (US); Suresh Pandey, Chelmsford, MA (US); Amy Gryshuk, Livermore, CA (US); Allan Oseroff, Buffalo, NY (US); Stephanie Pincus, legal representative, Buffalo, NY (US); Hani A. Nabi, Clarence, NY (US)

(73) Assignees: Health Research, Inc., Buffalo, NY (US); The Research Foundation of SUNY, Amherst, NY (US)

( * ) Notice: Subject to any disclaimer, the term of this patent is extended or adjusted under 35 U.S.C. 154(b) by 155 days.

(21) Appl. No.: 12/462,535

(22) Filed: Aug. 5, 2009

(65) Prior Publication Data

US 2010/0184970 A1   Jul. 22, 2010

Related U.S. Application Data

(63) Continuation-in-part of application No. 11/353,626, filed on Feb. 14, 2006, now abandoned.

(60) Provisional application No. 60/656,205, filed on Feb. 25, 2005.

(51) Int. Cl.
*C07B 47/00* (2006.01)
*C07D 487/22* (2006.01)
(52) U.S. Cl. ....................................................... 540/145
(58) Field of Classification Search .................. 540/145; 424/9
See application file for complete search history.

(56) References Cited

U.S. PATENT DOCUMENTS

| | | | |
|---|---|---|---|
| 6,114,321 | A  | 9/2000 | Platzek et al. |
| 6,534,040 | B2 | 3/2003 | Pandey et al. |
| 6,746,663 | B2 | 6/2004 | Sakata et al. |
| 7,097,826 | B2 | 8/2006 | Pandey et al. |

*Primary Examiner* — Paul V. Ward
(74) *Attorney, Agent, or Firm* — Michael L. Dunn (57) ABSTRACT

This invention describes a first report on the synthesis of certain $^{124}$I-labelled photosensitizers related to chlorines and bacteriochlorins with long wavelength absorption in the range of 660-800 nm. In preliminary studies, these compounds show a great potential for tumor detection by positron emission tomography (PET) and treatment by photodynamic therapy (PDT). The development of tumor imaging or improved photodynamic therapy agent(s) itself represent an important step, but a dual function agent (PET imaging and PDT) provides the potential for diagnostic body scan followed by targeted therapy.

3 Claims, 5 Drawing Sheets

Fig. 6

PORPHYRIN-BASED COMPOUNDS FOR TUMOR IMAGING AND PHOTODYNAMIC THERAPY

CROSS REFERENCE TO RELATED APPLICATIONS

This application is a continuation-in-part of U.S. patent application Ser. No. 11/353,626 filed Feb. 14, 2006 now abandoned, which in turn claims priority from U.S. Provisional Patent Application No. 60/656,205 filed Feb. 25, 2005.

STATEMENT REGARDING FEDERALLY SPONSORED RESEARCH

This invention was made with government support under Grant Numbers NIH 1R21 CA109914-01 and CA055791 awarded by the National Institute of Health. The government has certain rights in this invention.

BACKGROUND OF THE INVENTION

The use of radiometal-labeled complexes and biomolecules as diagnostic agents is a relatively new area of medicinal chemistry. Research into $^{99m}$Tc radiopharmaceutical was the beginning of the study of coordinate chemistry as it related to diagnostic imaging. Since then, the development of novel radiopharmaceuticals for early stage diagnosis remains as one of the active areas of functional imaging. In recent years, the imaging modalities widely used in nuclear medicine include gamma scintigraphy and positron emission tomography (PET). Gamma scintigraphy requires a radiopharmaceutical containing a nuclide that emits gamma radiation and a gamma camera or SPECT (single-photon emission tomography) camera capable of imaging the patient injected with a gamma-emitting radiopharmaceutical. The energy of the gamma photons is of great importance, since most gamma cameras are designed in the range of 100-250 KeV. Radionuclides that decay with gamma energies lower than this range produce too much scatter, while gamma energies >250 KeV are difficult to collimate, and in either case the images may not be of sufficient quality. PET requires a radiopharmaceutical labeled with a positron-emitting radionuclide ($\square^+$) and a PET camera for imaging the patient. Positron decay results in the emission of two 511 KeV photons 180° apart. PET scanners contain a circular array of detectors with coincidence circuits designed to specifically detect the 511 KeV photons emitted in opposite directions. Radiometal agents are also used to monitor various types of cancer therapy. In designing radiometal-based radiopharmaceuticals important factors to consider include the half-life of the radiometal, the mode of decay and the cost and the availability of the isotope. For diagnostic imaging, the half-life of the radionuclide must be long enough to carry out the desired chemistry to synthesize the radiopharmaceutical and long enough to allow accumulation in the target tissue in the patient while allowing clearance through the nontarget organs. Radiometals for radiopharmaceuticals used in PET and gamma scintigraphy range in half-life from about 10 min ($^{62}$Cu) to several days ($^{67}$Ga). The desired half-life is dependent upon the time required for the radiopharmaceutical to localize in the target tissue. For example, heart or brain perfusion-based radiopharmaceuticals require shorter half-lives, since they reach the target quickly whereas tumor-targeted compounds often take longer to reach the target for optimal target-to-background ratios to be obtained.

The design of a radiopharmaceutical agent requires optimizing the balance between specific in vivo targeting of the disease site (cancerous tumor) and clearance of radioactivity from non-target as well as the physical radioactive decay properties of the associated radionuclide. Several difficulties are encountered in the design of selective radiolabeled drug. These include problems related to efficient drug delivery, maximizing the residence time of the radioactivity at target sites, in vivo catabolism and metabolism of the drug, and optimization of relative rates if the radiolabeled drug or -metabolic clearance from non-target sites. Because of the multiple parameters that must be considered, developing effective radiopharmaceuticals for imaging and therapy of cancer is a complex problem that is not simply accomplished by attaching a radionuclide, in any fashion, to a non-radiolabeled targeting vector. The chemistry involved in the labeling process, therefore, is an integral and essential part of the drug design process. For example, if a radiometalated chelate is appended at some point to a biomolecular targeting entity, the structure and physiochemical properties of the chelate must be compatible with, and possibly even help promote, high specific uptake of the radiopharmaceutical at the diseased site. At the very least, this radiometal chelate should not interfere with pharmacokinetics, binding specificity or affinity to cancer cells. Clearly, the selection of the radionuclides, and the chemical strategies used for radiolabeling of molecules are critical elements if the formulation of safe and effective imaging/therapeutic agents.

For the last several years porphyrin-based compounds have been used for the treatment of cancer by photodynamic therapy (PDT). The concentration of certain porphyrins and related tetrapyrrolic systems is higher in malignant tumors than in most normal tissues and that has been the main reason to use these molecules as photosensitizers. Some tetrapyrrole-based compounds have been effective in a wide variety of malignancies, including skin, lung, bladder, head and neck and esophagus. The precise mechanism(s) of PDT are unknown; however, the in vivo animal data suggest that both direct cell killing and loss of tumor vascular function play a significant role.

Photodynamic therapy (PDT) exploits the biological consequences of localized oxidative damage inflicted by photodynamic processes. These critical elements are required for initial photodynamic processes to occur: a photosensitizer, light and oxygen. Superficial visible lesions, or those that are endoscopically accessible, e.g. endobronchial or esophageal tumors, are easily treated but the majority of malignant lesions are too deep to be reached by light of the wavelength required to trigger singlet oxygen production in the current generation of photosensitizers. Although the technology to deliver therapeutic light to deep lesions via optical fibers "capped" by a terminal diffuser is well developed, a deep lesion is by definition not visible from the skin surface and the PDT of deep tumors has thus far been impractical.

BRIEF DESCRIPTION OF THE INVENTION

In accordance with the invention, we have discovered a series of compounds that overcome the problems associated with methods in the prior art for radiation imaging of deep tumors. In particular, these compounds are $^{124}$I-phenyl derivatives of a chlorin, bacteriochlorin, porphyrin, pyropheophorbide, purpurinimide, or bacteriopupurinimide.

More particularly, preferred compounds of the invention include compounds of the formula:

or a pharmaceutically acceptable derivative thereof, wherein:

$R_1$ and $R_2$ are each independently substituted or unsubstituted alkyl, substituted or unsubstituted alkenyl, —C(O)$R_a$ or —COOR$_a$ or —CH(CH$_3$)(OR$_a$) or —CH(CH$_3$)(O(CH$_2$)—XR$_a$) where $R_a$ is hydrogen, substituted or unsubstituted alkyl, substituted or unsubstituted alkenyl, substituted or unsubstituted alkynyl, or substituted or unsubstituted cycloalkyl where $R_2$ may be CH=CH$_2$, CH(OR$_{20}$)CH$_3$, C(O)Me, C(=NR$_{20}$)CH$_3$ or CH(NHR$_{20}$)CH$_3$;

where X is an aryl or heteroaryl group;

n is an integer of 0 to 6;

where $R_{20}$ is methyl, butyl, heptyl, dodecyl or 3,5-bis(trifluoromethyl)-benzyl; and $R_{1a}$ and $R_{2a}$ are each independently hydrogen or substituted or unsubstituted alkyl, or together form a covalent bond;

$R_3$ and $R_4$ are each independently hydrogen or substituted or unsubstituted alkyl;

$R_{3a}$ and $R_{4a}$ are each independently hydrogen or substituted or unsubstituted alkyl, or together form a covalent bond;

$R_5$ is hydrogen or substituted or unsubstituted alkyl;

$R_6$ and $R_{6a}$ are each independently hydrogen or substituted or unsubstituted alkyl, or together form =O;

$R_7$ is a covalent bond, alkylene, azaalkyl, or azaaraalkyl or =NR$_{20}$;

$R_8$ and $R_{8a}$ are each independently hydrogen or substituted or unsubstituted alkyl or together form =O;

$R_9$ and $R_{10}$ are each independently hydrogen, or substituted or unsubstituted alkyl and $R_9$ may be —CH$_2$CH$_2$COOR$_a$ where $R_a$ is an alkyl group;

each of $R_a$-$R_{10}$, when substituted, is substituted with one or more substituents each independently selected from Q, where Q is alkyl, haloalkyl, halo, pseudohalo, or —COOR$_b$ where $R_b$ is hydrogen, alkyl, alkenyl, alkynyl, cycloalkyl, aryl, heteroaryl, araalkyl, or OR$_c$, where $R_c$ is hydrogen, alkyl, alkenyl, alkynyl, cycloalkyl, or aryl or CONR$_d$R$_e$ where $R_d$ and $R_e$ are each independently hydrogen, alkyl, alkenyl, alkynyl, cycloalkyl, or aryl, or NR$_f$R$_g$ where $R_f$ and $R_g$ are each independently hydrogen, alkyl, alkenyl, alkynyl, cycloalkyl, or aryl, or =NR$_h$ where $R_h$ is hydrogen, alkyl, alkenyl, alkynyl, cycloalkyl, or aryl, or is an amino acid residue;

each Q is independently unsubstituted or is substituted with one or more substituents each independently selected from $Q_1$, where $Q_1$ is alkyl, haloalkyl, halo, pseudohalo, or —COOR$_b$ where $R_h$ is hydrogen, alkyl, alkenyl, alkynyl, cycloalkyl, aryl, heteroaryl, araalkyl, or OR$_c$ where $R_c$ is hydrogen, alkyl, alkenyl, alkynyl, cycloalkyl, or aryl or CONR$_d$R$_e$ where $R_d$ and $R_e$, are each independently hydrogen, alkyl, alkenyl, alkynyl, cycloalkyl, or aryl, or NR$_f$R$_g$ where $R_f$ and $R_g$ are each independently hydrogen, alkyl, alkenyl, alkynyl, cycloalkyl, or aryl, or =NR$_h$ where $R_h$ is hydrogen, alkyl, alkenyl, alkynyl, cycloalkyl, or aryl, or is an amino acid residue.

with the proviso that the compound contains at least one Q containing a $^{124}$I-phenyl group.

These compounds provide high tumor absorption with appropriate radiological life for tumor imaging.

The invention also includes the method of using these compounds for imaging and simultaneously permit nuclear imaging guided implantation of optical fibers within deep tumors would enable to treat by PDT.

DETAILED DESCRIPTION OF THE INVENTION

On the basis of a study of a series of alkyl ether analogs of pyropheophorbide-a, we developed a relatively long wavelength absorbing photosensitizer, the 3-(1-hexyloxy)ethyl-derivative of pyropheophorbide-a 1 (HPPH). This compound is tumor-avid and currently in Phase I/II human clinical trials at the Roswell Park Cancer Institute. We investigated the utility of this compound as a "vehicle" by conjugation with mono- or di-bisaminoethanethiols (N$_2$S$_2$ ligand). The results obtained from in vivo biodistribution experiments indicated that the tumor/non-tumor uptake ratio of the drug depends on the time and tumor size. With time, the clearance of the HPPH-based compounds from tumor was found to be slower than from most of the non-tumor tissues. However, the short 6 h half-life of $^{99m}$Tc was found to be incompatible with 24-hour imaging time, suggesting that the use of a longer-lived isotope could provide a useful scanning agent. Another approach for developing an improved tumor-imaging agent could be to replace HPPH with those compounds that exhibit significantly higher tumor to non-tumor ratio. The synthesis of the related long-lived radionuclide could generate improved imaging and therapeutic (PDT) agents.

A compound that effectively functions both as an imaging agent and a photosensitizer creates an entirely new paradigm for tumor diagnosis and therapy. After peripheral intravenous injection of this compound, a patient can be scanned with a scanner. The location of the tumor site(s) can thus be defined, and, while the patient remains in the scanner, an interventional nuclear scientist can transcutaneously insert ultra-slim needles that can act as introducers for light-transmission fibers into the lesion(s). Because each fiber diameter is <400 microns, the introducer needles would produce negligible tissue damage. A light source can be coupled to the fibers, and PDT of the lesion(s) can be commenced, without any significant injury to other organs. Because the same molecule represents the contrast medium and the therapeutic medium, the lesion(s) can be continuously imaged during needle/fiber placement, without any ambiguity in terms of localization or "misregistration" of separate diagnostic/therapeutic images. This paradigm would make the low-toxicity and high efficacy of PDT available to virtually any location from the skull base to the floor of the pelvis.

Positron emission tomography (PET) is a technique that permits non-invasive use of positron labeled molecular imaging probes to image and assay biochemical processes at cellular function in living subject. Compared to single-photon-emission-computed tomography (SPECT), to produce tomographic images, PET is at least tenfold more sensitive. The short half-lives of the most commonly used positron emitting nuclides are not suitable for drugs with biological half lives in days. However, Iodine-124 is a positron emitter with a half-life of 4.2 days and is suitable for labeling probes with biological half lives of few days. This isotope has not been widely used because of the limited availability and complex decay scheme including several high-energy gamma rays. Pentlow et al. were the first to show that quantitative imaging with $^{124}$I is possible.

In our attempt to develop an efficient bifunctional diagnostic/therapeutic agent, we initially synthesized and evaluated certain pyropheophorbide analogs (derived from chlorophyll-a)-$N_2S_2$-$^{99m}$Tc conjugates (23). The in vivo biodistribution results suggested that the short 6 h half-life of $^{99m}$Tc is incompatible with the 24 h imaging time (the time for maximum uptake of the drug and therapy), suggesting that the use of a longer-lived isotope could provide a useful scanning agent. Therefore, our objective was to introduce $^{124}$I positron emitter to certain tumor-avid porphyrin-based photosensitizers containing iodobenzyl functionalities and investigate their utility in tumor imaging and photodynamic therapy.

There are several methods for labeling the compounds with iodine isotopes. Conversion of the cold iodo- to radioactive iodo- is possible, but the specific activity of the resulting product is low. It has been shown that in general iodine substituted at aliphatic chain is less stable than that present in aromatic structures. Therefore, we prepared a series of aromatic alkyl ethers and evaluated them for in vitro (RIF cells) and in vivo efficacy (RIF cells). Among a series of alkyl ether analogs with variable carbon units containing an iodophenyl group, the 3-devinyl-3-(1'-3"-iodobenzyloxy)ethyl pyropheophorbide-a (Scheme 1) in preliminary screening was found to be as effective as HPPH, a photosensitizer developed in our laboratory, and is at Phase II human clinical trials.

Examples of compounds of the invention are:

Pyropheophorbide-a

Purpurinimide

Bacteriopurpurinimide

Purpurinimides

Bacteriopurpurinimides where R is —COOH, —CO$_2$R$_3$, —CONHR$_4$, monosaccharide, disaccharide, polysaccharide, folic acid residue, or integrin antagonist; R$_1$, when present, is C$_1$-C$_{12}$ alkyl, R$_3$ is C$_1$-C$_{12}$ alkyl and R$_4$ completes an amino acid residue.

Figure 3:
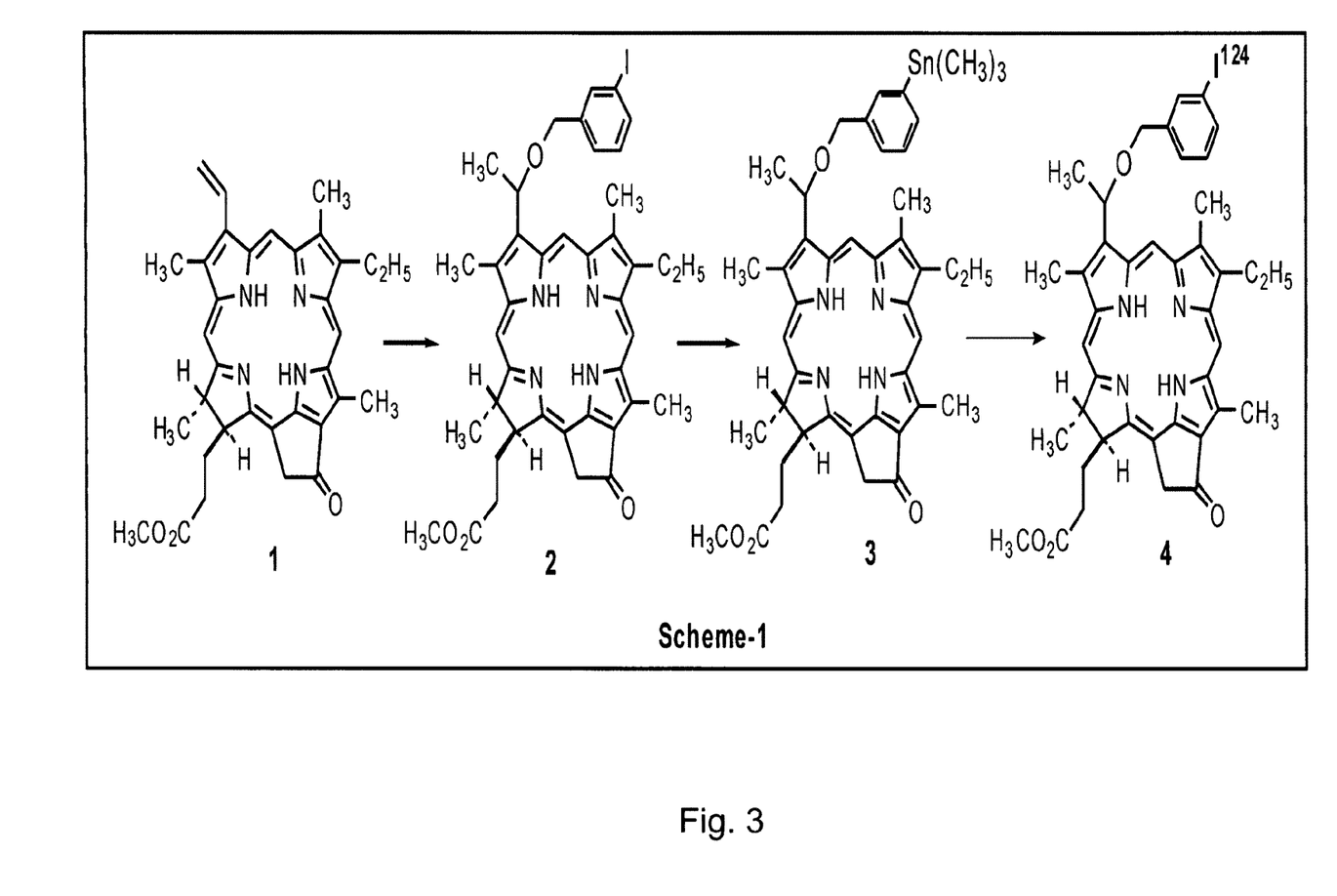
FIG. 3 shows a schematic diagram of preparation of compound of the invention (Scheme 1).

Methyl3-Devinyl-3-{1'-(3-iodobenzyloxy)ethyl pyropheophorbide a: As seen in FIG. 3, pyropheophorbide-a 1 was obtained from chlorophyll-a by following the literature procedure. It was reacted with HBr/acetic acid and the intermediate unstable bromo-derivative was immediately reacted with 3-iodobenzylalcohol under nitrogen atmosphere at room temperature for 45 min. After the standard work-up, the reaction mixture was purified by column chromatography (Alumina Gr. III, eluted with dichloromethane) and the desired iodo-derivative 2 was isolated in 70% yield. UV-vis(CH$_2$Cl$_2$): 662 (4.75×10$^4$), 536 (1.08×10$^4$), 505 (1.18×10$^4$), 410 (1.45× 10$^5$). $^1$H-NMR (CDCl$_3$; 400 MHz): □ 9.76, 9.55 and 8.56 (all s, 1H, meso-H); 7.76 (s, 1H, ArH); 7.64 (d, J=6.8, 1H, ArH); 7.30 (d, J=8.0, 1H, ArH); 7.05 (t, J=8.2, 1H, ArH); 6.00 (q, J=6.9, 1H, 3$^1$-H); 5.20 (dd(ABX pattern), J=19.6, 60.0, 2H, 13$^2$-CH$_2$); 4.70 (d, J=12.0, 1H, OCH$_2$Ar); 4.56 (dd, J=3.2, 11.6, 1H, OCH$_2$Ar); 4.48-4.53 (m, 1H, 18-H); 4.30-4.33 (m, 1H, 17-H); 3.72 (q, J=8.0, 2H, 8-CH$_2$CH$_3$); 3.69, 3.61, 3.38 and 3.21 (all s, all 3H, for 17$^3$-CO$_2$CH$_3$ and 3× ring CH$_3$); 2.66-2.74, 2.52-2.61 and 2.23-2.37 (m, 4H, 17$^1$ and 17$^2$-H); 2.18 (dd, J=2.8, 6.4, 3H, 3$^2$-CH$_3$); 1.83 (d, J=8.0, 3H, 18-CH$_3$); 1.72 (t, J=7.6, 3H, 8-CH$_2$CH$_3$); 0.41 (brs, 1H, NH); −1.71 (brs, 1H, NH). Mass: Calculated for C$_{41}$H$_{43}$N$_4$O$_4$I: 782. Found: 805 (M$^+$+Na).

Methyl-3-Devinyl-3-{1'-(3-tertbutyltinbenzyloxyethyl}pyropheophorbide a $^1$H-NMR (CDCl$_3$; 600 MHz): □ 9.76, 9.54 and 8.55 (all s, 1H, meso-H); 7.43 (m, 2H, ArH); 7.36 (m, 2H, ArH); 6.01 (q, J=6.7, 1H, 3$^1$-H); 5.20, dd (ABX pattern), J=19.1, 87.9, 2H, 13$^2$-CH$_2$); 4.78 (dd, J=5.4, 11.9, 1H, OCH$_2$Ar); 4.61 (dd, J=1.7, 12.0, 1H, OCH$_2$Ar); 4.50 (q, J=7.4, 1H, 18-H); 4.32 (d, J=8.8, 1H, 17-H); 3.72 (q, J=7.8, 2H, 8-CH$_2$CH$_3$); 3.69, 3.61, 3.37 and 3.18 (all s, all 3H, for 17$^3$-CO$_2$CH$_3$ and 3× ring CH$_3$); 2.66-2.75, 2.52-2.61 and 2.23-2.37 (m, 4H, 17$^1$ and 17$^2$-H); 2.16 (m, 3H, 3$^2$-CH$_3$); 1.83 (d, J=7.2, 3H, 18-CH$_3$); 1.72 (t, J=7.6, 3H, 8-CH$_2$CH$_3$); 0.45 (brs, 1H, NH); 0.19 (s, 9H, tert-butyltin); −0.59 (brs, 1H, NH). Mass: Calculated for C$_{45}$H$_{52}$N$_4$O$_4$Sn: 831. Found: 854 (M$^+$+Na).

Figure 1:
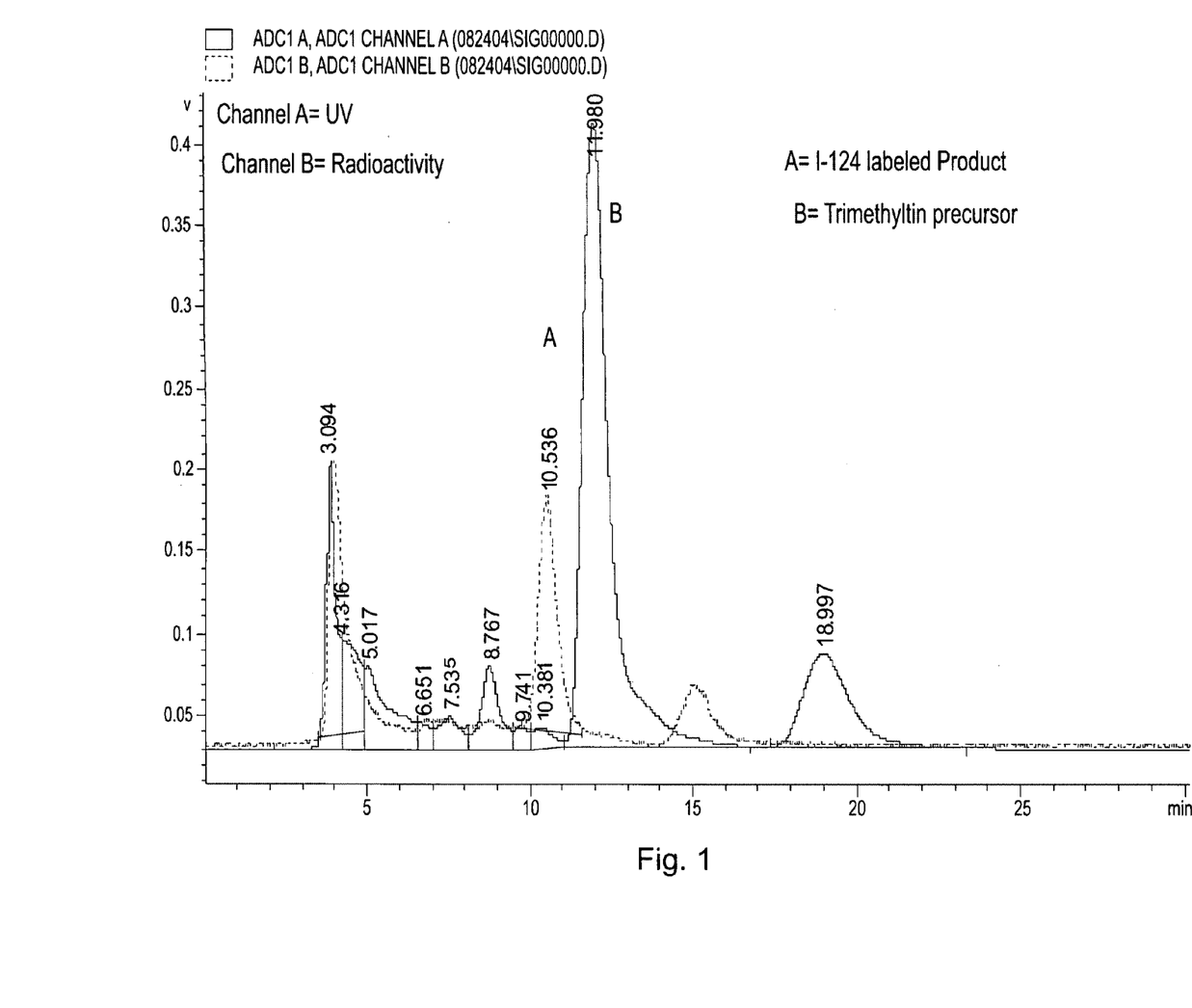
FIG. 1 shows the graph of an HPLC Chromatogram of reaction mixture on Maxsil C8 Column.
Figure 2:
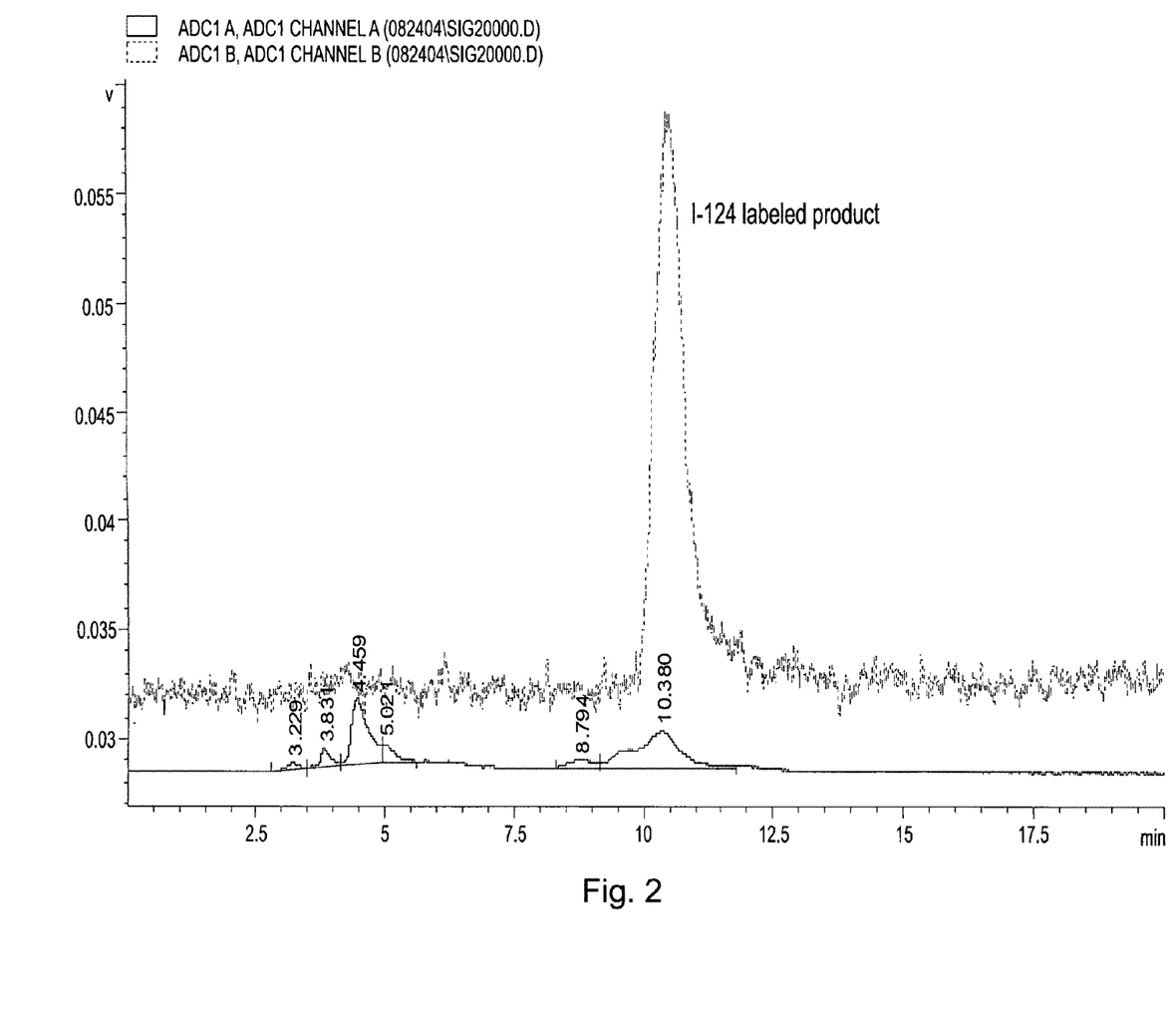
FIG. 2 shows the HPLC Chromatogram of purified labeled compound.

Preparation of $^{124}$I-labeled Photosensitizes:

The trimethyltin analog 3 (50 μg) obtained by reacting 2 with hexamethyldistannane and bis-(triphenylphosphine) palladium(II) dichloride in 1,4-dioxane (See FIG. 3) was dissolved in 100 μl of 10% acetic acid in methanol. Na$^{124}$I was added in 0.1N NaOH. The solution was mixed and an IODOGEN bead was added. The reaction mixture was incubated at room temperature for 30 minutes and the reaction product was purified using HPLC (FIG. 1). The labeled product was collected. The HPLC Chromatogram of the purified product is shown in FIG. 2.

Figure 4:
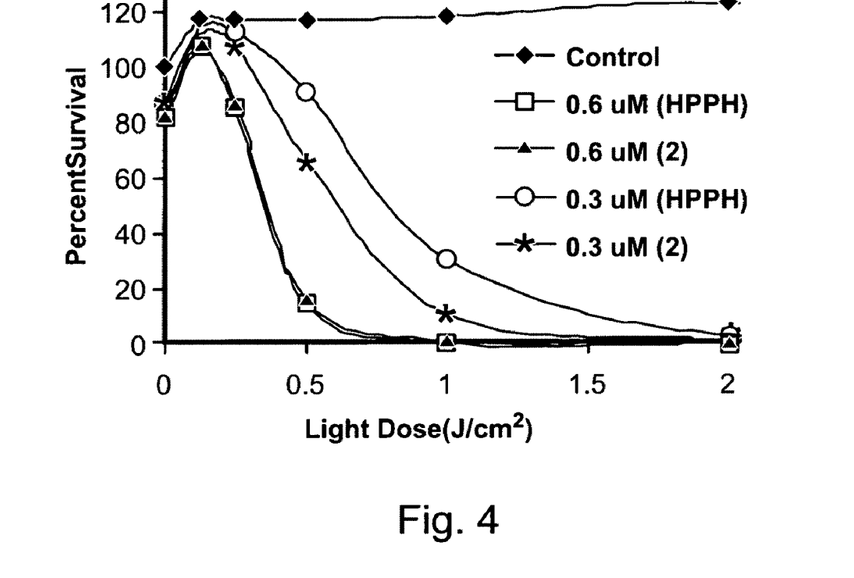
FIG. 4 shows a graph of percent survival versus light dose for comparative in vitro photosensitizing with iodo-analog at variable drug concentrations and light doses in RIF tumor cells.

For evaluating in vitro photosensitizing efficacy of 3-iodo-benxyloxyethyl-pyropheophorbide-a 2, RIF tumor cells were grown in alpha-DMEM with 10% fetal calf serum, penicillin and streptomycin. Cells were maintained in 5% CO$_2$, 95% air and 100% humidity. For determining the PDT efficacy, these cells were plated in 96-well plates and a density of 1×10$^4$ cells well in complete media. After overnight incubation to allow the cells to attach, the HPPH and the related cold-iodo derivative 2 were individually added at variable concentrations. After 3 hr incubation in the dark at 37° C., the cells were washed once with PBS, and irradiated with light. After light treatment, the cells were washed once and placed in complete media and incubated for 48 hrs. Then 10 μl of a 4-mg/ml solution of MTT was added to each well. After incubating for 4 hr at 37° C. the MTT+ media were removed and 100 μl DMSO was added to solubilize the formazin crystals. The 96-well plate was read on a microtiter plate reader at an absorbance of 560 nm. The optimal cell kill was obtained at a concentration of 1.00 □M. The results were plotted as percent survival of the corresponding dark (drug no light) control for each compound tested. (FIG. 4) Each data point represents the mean from 3 separate experiments, and the error bars are the standard deviation. Each experiment used 5 replicate wells.

Methyl-3-iodo-benzyloxy-ethyl)pyropheophorbide-a: The in vitro photosensitizing efficacy of HPPH and the iodo-benzyloxyethyl-pyropheophorbide-a 2 as seen in FIG. 3, was compared at variable experimental conditions and the results are summarized in FIG. 4. As can be seen both photosensitizers produced similar efficacy at 0.6 □M drug concentration. However, at lower concentration 0.30M the iodo-analog 2 was found to be slightly more effective.

Figure 5:
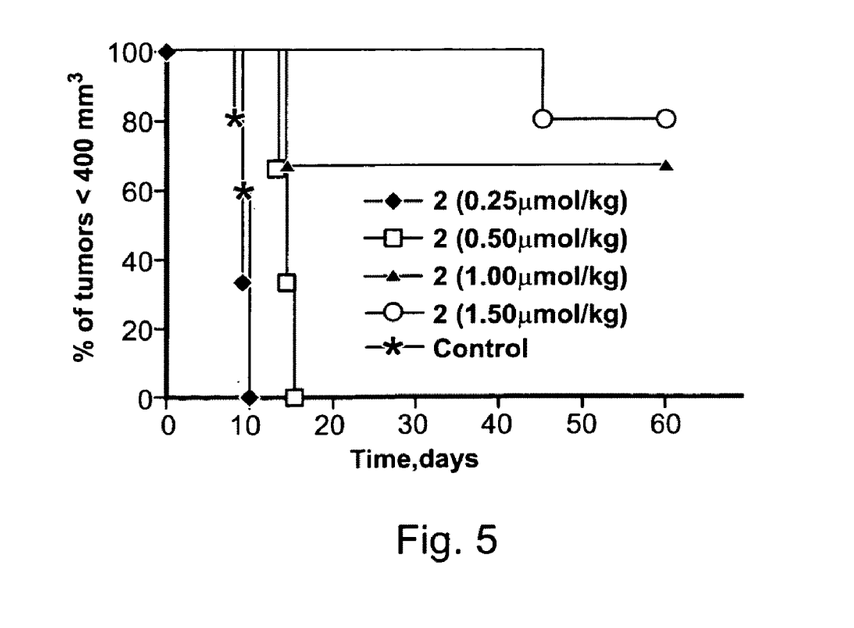
FIG. 5 shows a graph of percentage of tumors having a size less than 400 mm³ versus time in days after in vivo photosensitizing using 3-devinyl-3-(1'-iodobenzyloxy)ethyl analog "Compound 2" at variable concentrations for C3H mice implanted with RIF tumors exposed to laser light (665 nm, 135 J/cm², 75 mW/cm² for 30 minutes at 24 hours post injection of Compound 2.

In Vivo Photosensitizing Efficacy:

The in vivo efficacy was determined in C3H mice bearing RIF tumors (5 mice/group). The tumors were exposed to light at 665 nm (in vivo absorption) with a laser light (135 μm) for 30 minutes. The tumor-regrowth was measured everyday (for details see 'Methods' part of the project). As can be seen from FIG. 5, the 3-devinyl-3-(1'-iodobenzyloxy)ethyl analog was quite effective at a dose of 1.0 and 1.5 □mol/kg. At lower doses (0.25 and 0.50 □mole/kg), tumor re-growth was observed at 10 and 15 days post-injection. Further studies to optimize the treatment conditions at variable fluence and fluence-rates and time intervals are currently in progress.

Figure 6:
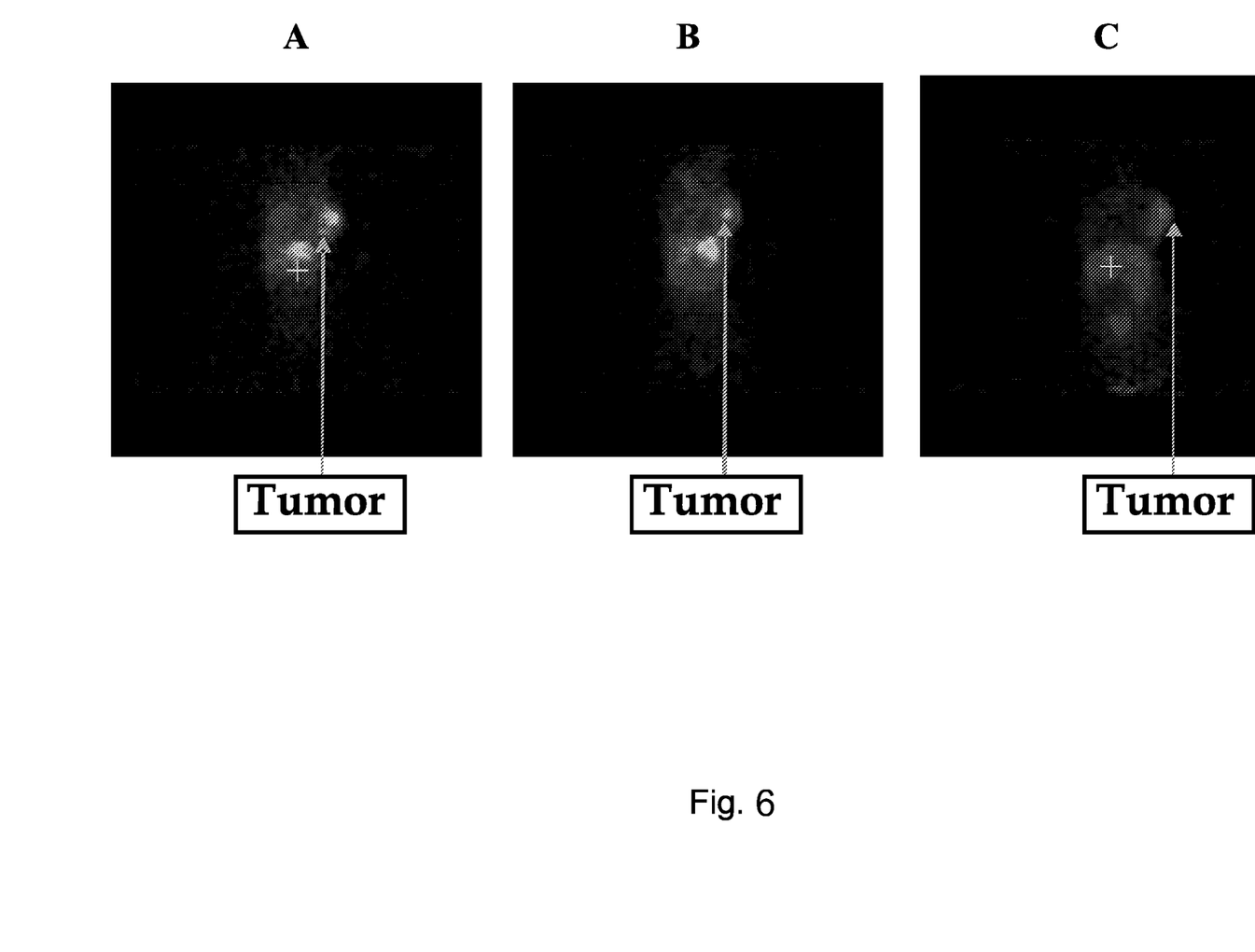
FIG. 6 shows PET tumor images of mice having RIF tumors injected with $I^{124}$ analog 4 (50 µCi) at (A) 24 hours, (B) 48 hours and (C) 72 hours post injection.

In Vivo Tumor Imaging:

In initial experiments, the 1-124 labeled photosensitizer 2 at variable radioactive doses (35, 50 and 100 □Ci) was injected in three sets of C3H mice (3 mice/group, bearing RIF tumors at the shoulder) respectively and the images were taken with a small animal PET scanner at 24, 48 and 72 h time intervals (FIG. 6 images A, B, and C). In all radioactive doses, the best images were obtained at 48 h post injection of the drug. However, as expected, the presence of the compound in some other organs, especially in liver was evident.

Biodistribution Studies:

After PET imaging at 48 h post-injection, a group of mice (3 mice/group) were sacrificed and the biodistribution of the I-124 PET agent in selected organs/gram were determined. The results are summarized in Table 1.

TABLE 1

Biodistribution results of I-124 labeled photosensitizer 4 in some selected organ of mice (3 mice/group) at 48 h post injection

| | Parts | | | | | | | | | |
|---|---|---|---|---|---|---|---|---|---|---|
| | Blood | Muscle | Spleen | Kidney | Lungs | Heart | Liver | Gut | Stomach | Tumor |
| Mouse 1 | 1.47 | 0.18 | 2.04 | 1.09 | 0.99 | 0.79 | 3.46 | 3.6 | 1.3 | 2.4 |
| Mouse 2 | 1.33 | 0.49 | 2.23 | 1.21 | 1.29 | 1.21 | 3.22 | 2.22 | 0.66 | 2.15 |
| Mouse 3 | 0.57 | 0.37 | 2.05 | 0.99 | 1.00 | 0.98 | 3.26 | 1.69 | 1.10 | 2.10 |
| AVG | 1.12 | 0.35 | 2.11 | 1.10 | 1.09 | 0.99 | 3.31 | 2.47 | 1.02 | 2.22 |
| Std Dev | 0.48 | 0.16 | 0.11 | 0.11 | 0.17 | 0.21 | 0.13 | 1.03 | 0.33 | 0.16 |

The imaging of specific molecular targets that are associated with cancer should allow earlier diagnosis and better management of oncology patients. Positron emission tomography (PET) is a highly sensitive non-invasive technology that is ideally suited for pre-clinical and clinical imaging of cancer biology, in contrast to anatomical approaches. By using radiolabelled tracers, which are injected in nonpharmacological doses, three-dimensional images can be reconstructed by a computer to show the concentration and location(s) of the tracer of interest. Compared to other positron emitters, I-124 has advantage due to its longer half-life (4.2 days). Our invention reports a first example for the preparation of I-124 labeled photosensitizers related to chlorines and bacteriochlorins with long wavelength absorption in the range of 660-800 nm. We have also shown the utility of these tumor-avid compounds for tumor detection and therapy. Our approach also provides an opportunity to develop target-specific bifunctional agents by targeting certain receptors known to have over-expression in tumors, and these studies are currently in progress.

We claim:

1. An $^{124}$I-phenyl compound of a chlorin, bacteriochlorin, porphyrin, pyropheophorbide, purpurinimide, or bacteriopourinimide having the formula:

or a pharmaceutically acceptable derivative thereof, wherein:

$R_1$ and $R_2$ are each independently substituted or unsubstituted alkyl, substituted or unsubstituted alkenyl, —C(O)$R_a$ or —COOR$_a$ or —CH(CH$_3$)(OR$_a$) or —CH(CH$_3$)(O(CH$_2$)$_n$XR$_a$) where $R_a$ is hydrogen, substituted or unsubstituted alkyl, substituted or unsubstituted alkenyl, substituted or unsubstituted alkynyl, or substituted or unsubstituted cycloalkyl where $R_2$ may be CH=CH$_2$, CH(OR$_{20}$)CH$_3$, C(O)Me, C(=NR$_{20}$)CH$_3$ or CH(NHR$_{20}$)CH$_3$;

where X is an aryl or heteroaryl group;

n is an integer of 0 to 6;

where $R_{20}$ is methyl, butyl, heptyl, dodecyl or 3,5-bis(trifluoromethyl)-benzyl; and $R_{1a}$ and $R_{2a}$ are each independently hydrogen or substituted or unsubstituted alkyl, or together form a covalent bond;

$R_3$ and $R_4$ are each independently hydrogen or substituted or unsubstituted alkyl;

$R_{3a}$ and $R_{4a}$ are each independently hydrogen or substituted or unsubstituted alkyl, or together form a covalent bond;

$R_5$ is hydrogen or substituted or unsubstituted alkyl;

$R_6$ and $R_{6a}$ are each independently hydrogen or substituted or unsubstituted alkyl, or together form =O;

$R_7$ is a covalent bond, alkylene, azaalkyl, or azaaraalkyl or =NR$_{20}$;

$R_8$ and $R_{8a}$ are each independently hydrogen or substituted or unsubstituted alkyl or together form =O;

$R_9$ and $R_{10}$ are each independently hydrogen, or substituted or unsubstituted alkyl and $R_9$ may be —$CH_2CH_2COOR_a$ where $R_a$ is an alkyl group;

each of $R_a$, $R_{1a}$-$R_{4a}$, $R_{6a}$, $R_{8a}$, $R_1$-$R_{10}$, when substituted, is substituted with one or more substituents each independently selected from Q, where Q is alkyl, haloalkyl, halo, or —$COOR_b$ where $R_b$ is hydrogen, alkyl, alkenyl, alkynyl, cycloalkyl, aryl, heteroaryl, araalkyl, or $OR_c$, where $R_c$ is hydrogen, alkyl, alkenyl, alkynyl, cycloalkyl, or aryl or $CONR_dR_e$ where $R_d$ and $R_e$ are each independently hydrogen, alkyl, alkenyl, alkynyl, cycloalkyl, or aryl, or $NR_fR_g$ where $R_f$ and $R_g$ are each independently hydrogen, alkyl, alkenyl, alkynyl, cycloalkyl, or aryl, or =$NR_h$ where $R_h$ is hydrogen, alkyl, alkenyl, alkynyl, cycloalkyl, or aryl, or is an amino acid residue;

each Q is independently unsubstituted or is substituted with one or more substituents each independently selected from $Q_1$, where $Q_1$ is alkyl, haloalkyl, halo, pseudohalo, or —$COOR_b$ where $R_b$ is hydrogen, alkyl, alkenyl, alkynyl, cycloalkyl, aryl, heteroaryl, araalkyl, or $OR_c$ where $R_c$ is hydrogen, alkyl, alkenyl, alkynyl, cycloalkyl, or aryl or $CONR_dR_e$ where $R_d$ and $R_e$ are each independently hydrogen, alkyl, alkenyl, alkynyl, cycloalkyl, or aryl, or $NR_fR_g$ where $R_f$ and $R_g$ are each independently hydrogen, alkyl, alkenyl, alkynyl, cycloalkyl, or aryl, or =$NR_h$ where $R_h$ is hydrogen, alkyl, alkenyl, alkynyl, cycloalkyl, or aryl, or is an amino acid residue;

with the proviso that the compound contains at least one Q containing a $^{124}$I-phenyl group.

2. An $^{124}$I-phenyl compound of a pyropheophorbide, purpurinimide, or bacteriopupurinimide selected from the group consisting of:

Pyropheophorbide-a

Purpurinimide

Bacteriopurpurinimide

Purpurinimides

Bacteriopurpurinimides where R is —COOH, —CO$_2$R$_3$, —CONHR$_4$, or folic acid residue; R$_1$, when present, is C$_1$-C$_{12}$ alkyl, R$_3$ is C$_1$-C$_{12}$ alkyl and R$_4$ completes an amino acid residue.

3. The pyropheophorbide a of claim 2 where R is —CO$_2$R$_3$.

* * * * *

UNITED STATES PATENT AND TRADEMARK OFFICE
CERTIFICATE OF CORRECTION

PATENT NO.        : 8,198,432 B2                                    Page 1 of 1
APPLICATION NO.   : 12/462535
DATED             : June 12, 2012
INVENTOR(S)       : Ravindra K. Pandey et al.

It is certified that error appears in the above-identified patent and that said Letters Patent is hereby corrected as shown below:

In the STATEMENT REGARDING FEDERALLY SPONSORED RESEARCH,
Column 1, line 14, delete, "This invention was made with government support under Grant Numbers NIH 1R21 CA109914-01 and CA055791 awarded by the National Institute of Health. The government has certain rights in this invention."
and insert,
--This invention was made with government support under CA109914, CA055791 and CA114053 awarded by National Institutes of Health. The government has certain rights in the invention.--

Signed and Sealed this
Twenty-third Day of October, 2012

David J. Kappos
*Director of the United States Patent and Trademark Office*